(12) United States Patent
Willson, III et al.

(10) Patent No.: US 7,569,347 B2
(45) Date of Patent: *Aug. 4, 2009

(54) APPARATUS, METHODS AND COMPOSITIONS FOR BIOTECHNICAL SEPARATIONS

(75) Inventors: Richard C. Willson, III, Houston, TX (US); Richard Don Goodin, Austin, TX (US)

(73) Assignee: Technology Licensing Co. LLC, Palm Harbor, FL (US)

( * ) Notice: Subject to any disclaimer, the term of this patent is extended or adjusted under 35 U.S.C. 154(b) by 317 days.

This patent is subject to a terminal disclaimer.

(21) Appl. No.: 11/345,252

(22) Filed: Feb. 1, 2006

(65) Prior Publication Data

US 2006/0141521 A1 Jun. 29, 2006

Related U.S. Application Data (63) Continuation-in-part of application No. 09/841,763, filed on Apr. 24, 2001, now abandoned, which is a continuation-in-part of application No. 09/609,996, filed on Jul. 3, 2000, now Pat. No. 6,617,108.

(60) Provisional application No. 60/849,896, filed on Feb. 3, 2005, provisional application No. 60/143,768, filed on Jul. 12, 1999.

(51) Int. Cl.
*C12Q 1/68* (2006.01)
(52) U.S. Cl. .......................................................... 435/6
(58) Field of Classification Search ................. 435/91.2
See application file for complete search history.

(56) References Cited

U.S. PATENT DOCUMENTS 3,867,286 A * 2/1975 Quinlan ...................... 210/700
6,063,604 A * 5/2000 Wick et al. ................. 435/91.2
2003/0059769 A1* 3/2003 Parma et al. .................... 435/6

OTHER PUBLICATIONS

Ahokas et al. PCR Methods and Applicant, vol. 3, pp. 65-68, 1993.*
Frugier et al. Nucleic acids Research, vol. 22, No. 14, pp. 2784-2790, 1994.*

* cited by examiner

*Primary Examiner*—Gary Benzion
*Assistant Examiner*—Cynthia B Wilder
(74) *Attorney, Agent, or Firm*—Richard Coale Willson, Jr.

(57) ABSTRACT

RNA, preferably messenger RNA, is purified by use of selective precipitation, preferably by addition of compaction agents. Also included is a scalable method for the liquid-phase separation of DNA from RNA and RNA may also be recovered by fractional precipitation. Specific classes of compounds e.g. phase transfer catalysts (PTCs), most preferably selected polyamines of U.S. Pat. No. 6,617,108 polyamines which are quaternary compounds are unexpectedly potent in causing selective precipitation of DNA away from RNA, at low concentrations and in the presence of relatively elevated ionic strength selective removal of DNA can also remove both RNA and DNA, leaving behind a mixture which is advantageous for the further purification of, e.g., proteins. The invention include mini-preps, preferably of RNA or of plasmid and chromosomal DNA to obtain sequenceable and restriction digestible DNA in high yields in multiple simultaneous procedures and/or enhanced stripping of the compaction agent by a stripping method comprising high salt addition and pH shift, and combinations of these techniques. Isolation of RNA from bacterial lysates can employ selective precipitation by compaction agents.

20 Claims, 3 Drawing Sheets

An⁻

STRUCTURE I

Figure 1. Structure of preferred compaction agents (see Specification for definitions).

Figure 2. Structure of Quatroquat

Figure 3. Structure of PZ-6 (quatrodiquat)

Figure 4. Precipitation of Salmon Sperm DNA by PZ6.

Figure 5

APPARATUS, METHODS AND COMPOSITIONS FOR BIOTECHNICAL SEPARATIONS

The present application claims priority of U.S. provisional patent application 60/849,896 filed Feb. 3, 2005 and is a continuation-in-part of U.S. patent application Ser. No. 09/841,763 filed Apr. 24, 2001 now abandoned which is itself a continuation-in-part of 09/609,996 filed Jul. 3, 2000, now U.S. Pat. No. 6,617,108 granted 9 Sep. 2003, which itself has priority of U.S. Provisional Application 60/143,768 filed Jul. 12, 1999.

BACKGROUND OF THE INVENTION

I. Field of the Invention

The present invention relates to the general field of biochemical assays and separations, and to apparatus for their practice, generally classified in U.S. Patent Class 435.

II. Description of the Prior Art

Interest in nucleic acid purification and assays has increased with human trials of plasmid-based vaccines (e.g., for influenza, HIV, and malaria) and therapeutics (e.g., insulin and vascularization promoters) as well as the steady expansion of DNA sequencing activities, pharmacogenomics, and genetic testing. This invention embodies a rapid and efficient method of nucleic acid assay using selective precipitation by compaction agents.

Prior Art will include the following:

Murphy, J. C., Wibbenmeyer, J. A., Fox, G. E., and Willson, R. C. (1999) Purification of plasmid DNA using selective precipitation by compaction agents. Nature Biotechnol. 17, 822-823.

Murphy, J. C., G. E. Fox and R. C. Willson, "RNA Isolation and Fractionation using Compaction Agents," Analytical Biochemistry, 295, 143 (2001).

Mourich D. V., Munks M. W., Murphy J. C., Willson R. C., and Hill A. B., "Spermine compaction is an efficient and economical method of producing vaccination-grade DNA", J. Immunol. Methods. 274:257-264 (2003).

DeWalt, B., Murphy, J. C., Fox, G. E., and Willson, R. C., "Compaction Agent Clarification of Microbial Lysates", Protein Expression and Purification, 28(2) 220-223 (2003).

Related U.S. Pat. No. 6,617,108 describes and claims processes for purification of DNA and separation of proteins, etc. by adding a compaction agent e.g. basic polypeptides, polyamines, trivalent and tetravalent metal ions to the mixture. This present application embodies the discovery that unexpectedly superior results are obtained by use of selected compaction agents e.g. quaternary ammonium compounds and the phosphonium-based catalysts. Preferred compaction agents include quaternary ammonium polyamines, the compounds of FIGS. 1-3. Tables B, C and D show some examples of these compounds.

In the literature, "q-value" and "C#" are useful parameters for correlating reactivity and selectivity. The q-value was proposed by Marc Halpern (PTC Organics) in 1988 and reflects the accessibility of the positive charge of a quat. A q-value of 1.0 to 2.0 often gives high reactivity for "transfer rate limited" reactions whereas a q-value of <1 often gives high reactivity for reactions which require a loose ion pair. The q-value is calculated by adding the reciprocals of the numbers of carbons on each of the 4 chains. C# is simply the sum of all of the carbons of the quat and is a measure of the organophilicity of the quat. Sources include Sachem, Cognis, Lion Akzo, Merck and PTC organics, whose websites give additional information.

III. Problems Presented by Prior Art

Most current methods of nucleic acid separation are relatively time-consuming and require the use of adsorbents, toxic substances, nucleases, and/or filtration media to separate individual nucleic acid types from protein, genomic DNA, endotoxins and especially the abundant RNA present in cell lysates. Many do not provide samples in a state ready for assays such as RT-PCR.

The present invention offers several important improvements over current methods: no DNAse and/or other enzymes need be used, the technique requires no chromatographic medium, and the purified samples are left in a form ready for assays such as RT-PCR. Also, with the use of different compaction agents, different types of nucleic acids can be separated from the same mixture. The invention can separate different types of RNA and DNA as long as some secondary structure is present.

In addition, RNA can be fractionated based on molecular weight via selective precipitation.

The method can also be used for parallel purification of a large number of samples (mini-preps) and is readily adaptable to automation (robotics).

In a preferred embodiment, the invention also provides a method for making a biochemical assay of one or more selected messenger RNA (mRNA) species, while reducing the RT-PCR background due to genomic DNA contamination.

The invention also provides a method of preparing a nucleic acid sample having reduced DNA content and also reduced content of compaction precipitation agent by selective removal of compaction agent.

Especially preferred embodiments include selective DNA precipitation over RNA, assay of RNA by first precipitating DNA, then assaying RNA in a second step; syntheses of preferred compaction precipitation agents; and removal of compaction agents before performing biochemical assays on the sample.

SUMMARY OF THE INVENTION

The invention comprises a method of assaying RNA in a mixture comprising DNA and RNA, said method comprising in combination the steps of:

A. adding a compaction agent to effect compaction precipitation; and

B. adding an enzyme to catalyze a reaction; and

C. detecting a product of the reaction catalyzed by the enzyme.

The invention further comprises a method of preparing substantially purified RNA without the use of nucleases or proteases, or organic solvent extraction, comprising adding an effective amount of a compaction agent selected from the group consisting of: quaternary ammonium polyamines and Phase Transfer Catalysts (PTCs) to a lysate containing DNA and RNA to selectively precipitate from said lysate, plasmid-DNA, chromosomal-DNA, or oligonucleocidal-DNA having a content of RNA of less than 3% by weight.

Compositions of the invention comprise a mixture comprising RNA, DNA, a compaction precipitation agent, and a reverse transcriptase or DNA polymerase enzyme.

General Statement of the Invention

According to the invention, in preferred embodiments, DNA, preferably plasmid DNA, is readily purified, by use of selective precipitation, preferably by addition of compaction agents. Also, included is a scaleable method for the liquid-phase separation of DNA from RNA. RNA may also be recovered by fractional precipitation according to the invention.

We have discovered that RNA, commonly present mixed with DNA, can be left in solution while DNA is directly precipitated. DNA can be re-dissolved by addition of salts, excursions of pH, and/or removal of compaction agent.

Treatment of protein-containing samples with compaction agents to remove nucleic acids facilitates subsequent protein purification.

Additional aspects of the invention include mini-preps, preferably of plasmid and chromosomal DNA to obtain sequenceable and restriction digestible DNA in high yields in multiple simultaneous procedures.

Still further aspects comprise removal of the compaction agent by a stripping method comprising high salt addition or pH shift, and combinations of these techniques.

Also, disclosed is a method of assay in which DNA is removed from RNA species of interest by selective precipitation, optionally followed by treatment with an enzyme such as a reverse transcriptase and/or polymerase.

Each of these parameters is discussed below:

Cell Mass: The starting material is often a mass of cells prepared by fermentation or cell culture, isolated from the environment or a patient, or derived from tissues. Viruses may be present, and viral RNA may be of primary interest in some preferred applications. The cells are then disrupted so the nucleic acids go into solution, forming a lysate. A variety of cell types can be used as feed for this process, with human, non-human primate, rodent, bacterial, yeast, other eukaryotic, Gram-negative and Gram-positive being preferred, and human, virus, rodent, and non-human primate being most preferred.

Product: The product of the invention can be a protein-containing mixture depleted of nucleic acids, purified DNA, RNA such as messenger RNA, viral RNA, ribosomal RNA or microRNA; or assay results, preferably RNA, and most preferably a sample containing RNA with reduced content of DNA.

In general, the selective precipitation of the invention can be applied to all bacteria (Gram-negative, Gram-positive and Archaea), all eukaryotes (such as yeast and human cells), recombinant cells, viruses and all synthetic nucleic acids.

Compaction Agents: The compaction agents are preferably small, cationic molecules, which bind in either the major or minor grooves of a double-stranded RNA or DNA molecule, reducing the volume occupied by the nucleic acid. Compaction agents include those selected from the group consisting of: quaternary ammonium polyamines, the compounds of FIGS. 1-3 and PTCs.

While not to be bound by any theory, it appears compaction of DNA involves charge neutralization in combination with stabilization of inter-helix interactions. The compaction agent binds in either the major or minor groove, in proximity to the negatively charged phosphate groups. Precipitation occurs when adjacent DNA helices are affected simultaneously, with the compaction agent not only reducing the helix-helix repulsion but also bridging the helixes. Hoopes described this phenomenon in 1981 but upon further investigation, we have discovered that RNA is far less readily precipitated by certain compaction agents, preferably linear polyamine type compaction agents, and found that RNA can be selectively precipitated and even fractionated using specialized compaction agents, most preferably, hexammine cobalt as the compaction agent and/or without substantial precipitation of contaminating endotoxins.

Figure 1:
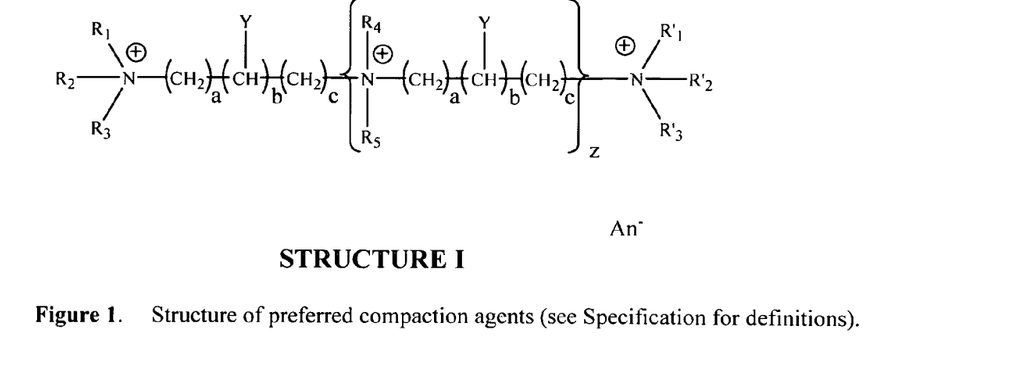
FIG. 1 shows the generic structure of one class of preferred compaction agents.
Figure 2:
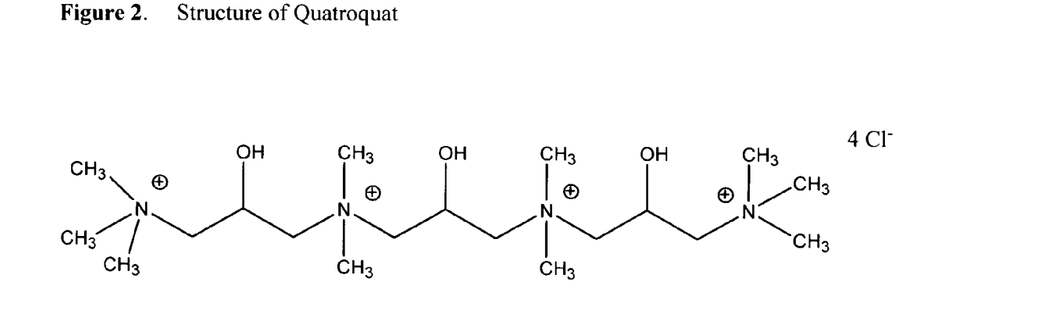
FIG. 2 shows the structure of one class of more preferred compaction agents.
Figure 3:
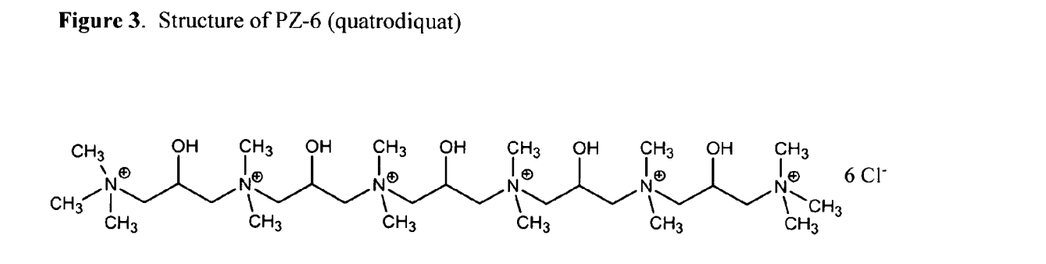
FIG. 3 shows the generic structure of one class of most preferred compaction agents.

In general, there will be added about 0.001 to 20, more preferably about 0.01 to 5 and most preferably about 0.03 to 1 mM of a compaction agent, preferably selected from the group consisting of: basic polypeptides (e.g. polylysine), polyamines (e.g. protamine, spermidine, spermine, putrescine, cadaverine, etc.), trivalent and tetravalent metal ions (e.g. hexammine cobalt, chloropentammine cobalt, chromium (III)), netropsin, distamycin, lexitropans, DAPI (4',6 diamino 2-phenylindol), berenil, pentamidine, manganese chloride.), quaternary ammonium polyamines, the compounds of FIGS. 1-3 and PTCs. At present knowledge, the quaternary ammonium polyamines, the compounds of FIGS. 1-3 and PTCs will be more preferred, but any other molecule that can be used to compact DNA via the mechanism described above can be used according to the product to be produced and the cell mass available.

Many other agents may be considered compaction agents and these include: basic polypeptides (i.e. polylysine), polyamines (i.e. protamine, spermidine, spermine, cadaverine, etc.), trivalent and tetravalent metal ions (i.e. hexammine cobalt, chloropentammine cobalt, chromium (III)), netropsin, distamycin, lexitropans, DAPI (4',6 diamino 2-phenylindol), berenil, pentamidine, manganese chloride, or any other molecule that can be used to compact DNA via the mechanism described above. Also any protein having multiple binding domains for nucleic acids can potentially, for large complexes, result in the precipitation of nucleic acids.

Alternating Bonds

Particularly preferred are compaction precipitation agents having at least 4 and less than 30 (preferably 8 to 20) positively charged groups, which groups are separated by 2-6 (preferably 3-4) covalent bond linkages.

Preferred compaction agents include those having the formula shown in FIG. 1, and those shown in FIGS. 2 and 3 with Quatroquat and Q-diquat (See Example 2) being most preferred.

The preferred polyquaternary ammonium compounds of the instant invention include those having the structure (1):

STRUCTURE I

An⁻

[See FIG. 1]

wherein
- each group $R_1$, $R_2$, $R_3$, $R'_1$, $R'_2$, $R'_3$, $R_4$ and $R_5$ may be independently selected from alkyl, aryl, and aralky, and each preferably contains 1-10, more preferably 1-6 carbon atoms;
- each Y may be independently selected from —H, —OH, halo, alkyl, aryl and aralkyl; and each preferably contains 0-10, more preferably 0-6 carbon atoms;
- z may be any whole number from 0 to about 10; more preferably 0-6;
- a, b, and c each may be any whole number from 0 to 2, with the proviso that the sum a+b+c in any fragment is at least 1; and
- An⁻ may be one of more organic or inorganic, monovalent or polyvalent anion as needed to obtain a neutral compound e.g. chloride, hydroxide, acetate.

Preferred Compaction Agent Selectivities

We have found that spermidine has high potency for the condensation of plasmid DNA and chromosomal DNA but not RNA, hexammine cobalt has a relatively broad scattering curve for total RNA, suggesting the possibility of fractionation, and spermine has a high potency for all three nucleic acids. These scattering curves were earlier used as the basis of a multi-step selective precipitation protocol for RNA in which plasmid DNA and chromosomal DNA are removed with an initial spermidine precipitation, RNA is precipitated or fractionated with a hexammine cobalt precipitation, and small RNAs (<500 bases) can be precipitated at increased hexammine cobalt concentration. Selective precipitation shows promise for separation of RNA without the use of enzymes, organic solvents, or gel electrophoresis. Large structured RNA molecules can be separated and RNA fractionated based on size and structure in solution phase.

More recently, we have found that quaternary ammonium polyamines, and the compounds of FIGS. 1-3 have enhanced potency for precipitation of DNA away from RNA, at lower concentrations and/or at higher ionic strength than previously reported agents. This is advantageous in the preparation of DNA, and in the preparation of RNA depleted of contaminating DNA, with the use of lower concentrations of compaction agent, especially in the presence of higher ionic strengths as may be found in cell lysates, physiological specimens, and the products of the widely-used alkaline lysis process.

II. Utility of the Invention

The present invention is useful in the separation of DNA from RNA and vice versa, and in preparing samples for assay of RNA species by reducing the content of related DNA species which can interfere with the assay. The invention is useful for producing proteins, RNA, messenger-RNA (mRNA), gRNA, miRNA, DNA, pDNA, and assays thereof.

Table A gives preferred, more preferred, and most preferred levels of some of the parameters of the invention.

Tables B and Table C list other preferred compaction agents.

DESCRIPTION OF THE PREFERRED EMBODIMENTS

EXAMPLE 1

RNA/DNA Compaction Separation

An *E. coli* alkaline lysate is preconditioned by an 8-fold dilution with water, and a quaternary ammonium compound; Quatro-diquat, available from SACHEM, (See Example 3) is added in a concentration of 30 uM to 40 uM, and precipitated the plasmid DNA much more than the RNA, producing a supernatent liquid enriched in RNA and a precipate (pellet) enriched in DNA. Upon checking the supernatants on an agarose electrophoresis gel, above 30 uM the plasmid band is missing, while the characteristic smear of RNA is still present.

This means Q-dQ and other quats are unexpectedly superior for plasmid purification. One of their key advantages is that the alkaline lysate needs only to be diluted to lower the ionic strength, and then the plasmid can be directly precipitated.

Compaction precipitation with poly quats is also compatible with good applicability in RT-PCR. It can remove genomic DNA effectively, leaving the great majority of the RNA in solution. Care is to be taken so that the precipitant does not interfere with the enzymes.

In protein purification processes, similar compaction separation techniques can remove nucleic acids to valuably facilitate the later steps of purification.

EXAMPLE 2

Synthesis of Quatroquat

Dimapol [1,3-bis(dimethylamino)-2-propanol] (1 mol) is mixed with stirring with 1 mole 1-chloro-3-trimethylammonium-2-propanol chloride. Temperature rises to about 30 degrees Celsius. After one hour, an additional 1.4 moles of 1-chloro-3-trimethylammonium-2-propanol chloride and some water are added. After 12 hours at 25 degrees Celsius, the temperature is increased to 50 degrees Celsius and held for 1.5 hours.

EXAMPLE 3

Synthesis of PZ-6 (Quatrodiquat)

Dimapol [1,3-bis(dimethylamino)-2-propanol] (2 mol) is added to 360 g water with stirring. 2 moles of Reagens [1-chloro-3-trimethylammonium-2-propanol] is added over three hours, keeping the temperature below 25 degrees Celsius by cooling. After 6 hours the reaction is complete. 1,3-dichloro-2-propanol (1 mol) is added over 1 hour. The solution is heated to 50 degrees Celsius for three hours. Chloride determination indicated the reaction is complete.

EXAMPLE 4

Compaction/RT-PCR mRNA Assay

A series of time-point samples of HeLa cells is subjected to RNA isolation by standard commercial methods which leave significant contaminating genomic DNA. An aliquot of each RNA sample is treated with 60 uM triquat-A (Sachem), aged 10 minutes, and centrifuged. The supernatant of each is subject to RT-PCR analysis for expression of a particular mRNA of interest.

EXAMPLE 5

Compaction/Removal/RT-PCR mRNA Assay

A series of time-point samples of drug-candidate-treated Baby Hamster Kidney cells is subjected to RNA isolation by standard commercial methods which leave significant contaminating genomic DNA. An aliquot of each RNA sample is treated with the quatro-diquat of Example 1 (Sachem), aged 10 minutes, and centrifuged. The supernatant of each is contacted with the cation-exchange adsorbent Bio-Rad Uno-Sphere S to reduce the concentration of compaction agent, and then subjected to RT-PCR analysis for expression of a particular mRNA of interest.

EXAMPLE 6

Compaction/Dilution/RT-PCR mRNA Assay

A series of time-point samples of pathogen-infected mouse tissue samples is subjected to RNA isolation by standard commercial methods which leave significant contaminating genomic DNA. An aliquot of each RNA sample is treated with a compaction agent (Sachem), aged 10 minutes, and centrifuged. The supernatant of each is diluted five-fold to reduce the concentration of compaction agent, and then subjected to RT-PCR analysis for expression of a particular mRNA of interest.

EXAMPLE 7

Compaction/Filtration/RT-PCR mRNA Assay

A series of time-point samples of drug-candidate-treated Baby Hamster Kidney cells is subjected to RNA isolation by standard commercial methods which leave significant contaminating genomic DNA. An aliquot of each RNA sample is treated with a compaction agent, aged 10 minutes, and filtered. The filtrate of each is subjected to RT-PCR analysis for expression of a particular mRNA of interest.

EXAMPLE 8

Compaction/Filtration/RT-PCR miRNA Assay

A series of time-point samples of cells from a murine liver regeneration model is subjected to RNA isolation by standard commercial methods which leave significant contaminating genomic DNA. An aliquot of each RNA sample is treated with a compaction agent, aged 10 minutes, and filtered. The filtrate of each is subjected to PCR-based analysis for expression of a particular microRNA of interest.

EXAMPLE 9

Clinical Compaction/RT-PCR Multiple mRNA Assay/Comparative

A sample of white blood cells from a leukemia patient is subjected to cell lysis. An aliquot of each sample is treated with 100 micromolar Quatroquat (Sachem), aged 10 minutes, and centrifuged. The supernatant of each is subject to RT-PCR analysis for expression of four different mRNAs, and the results used to select the course of treatment. An identical treatment with spermidine produces unusable results because of high residual genomic DNA contamination.

EXAMPLE 10

Plasmid Survives Lysis

A culture of *E. coli* bacteria harboring a 6 kilobase plasmid encoding expressing a recombinant form of beta-interferon is suspended in a solution containing 50 micromolar quatroquat and subjected to mechanical lysis using a French press at an average operating pressure of 8,000 psi. A substantial fraction of the plasmid survives lysis and is recovered from the lysates by resuspenstion and chromatography.

EXAMPLE 9

Clinical Compaction/RT-PCR Multiple mRNA Assay/Comparative

A sample of white blood cells from a leukemia patient is subjected to cell lysis by a method which leaves the sample at relatively high ionic strength. An aliquot of each sample is treated with 80 micromolar Quatroquat (Sachem), aged 10 minutes, and centrifuged. The supernatant of each is subject to RT-PCR analysis for expression of four different mRNAs, and the results used to select the course of treatment. An identical treatment with spermidine produces unusable results because the precipitant is not effective at higher ionic strength.

EXAMPLE 11

Better Lysate

A culture of E. coli bacteria expressing a recombinant form of beta-interferon is subjected to mechanical lysis using a French press at an average operating pressure of 8,000 psi, the lysate is diluted with water and 30 micromolar PZ-6 (quatrodiquat) is added to precipitate E. coli nucleic acids to facilitate subsequent purification of the expressed protein. The resulting treated lysates is lower in viscosity and has fewer anion-exchanger-occupying nucleic acids than an identical lysates treated with 30 mM spermine.

EXAMPLE 12

Precipitation of DNA with PZ6

A solution of Salmon DNA (Sigma-Aldrich) was prepared in 25 mM MOPSO buffer, pH 6.8 at a concentration of 50 micrograms per mL. NaCl concentration was adjusted to 30 mM. By adding increasing amounts of PZ6 from a 10 mM stock solution in the same buffer (accounting for dilution), a titration curve for the precipitation of DNA by PZ6 was acquired. Each point was a separate determination using a fresh solution of DNA. The DNA in solution was determined by measuring the UV-visible absorbance at 258 nm. The solutions were spun down at 9,000 g to remove the precipitated DNA from solution before measuring the absorbance.

Figure 4:
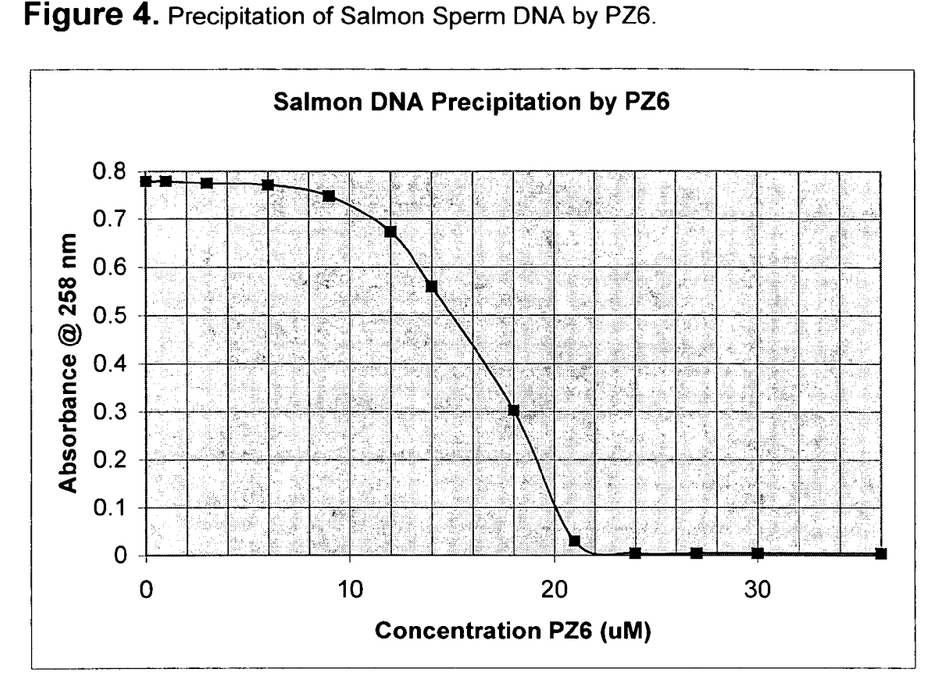
FIG. 4 shows precipitation of salmon sperm DNA with a preferred compaction agent.
Figure 5:
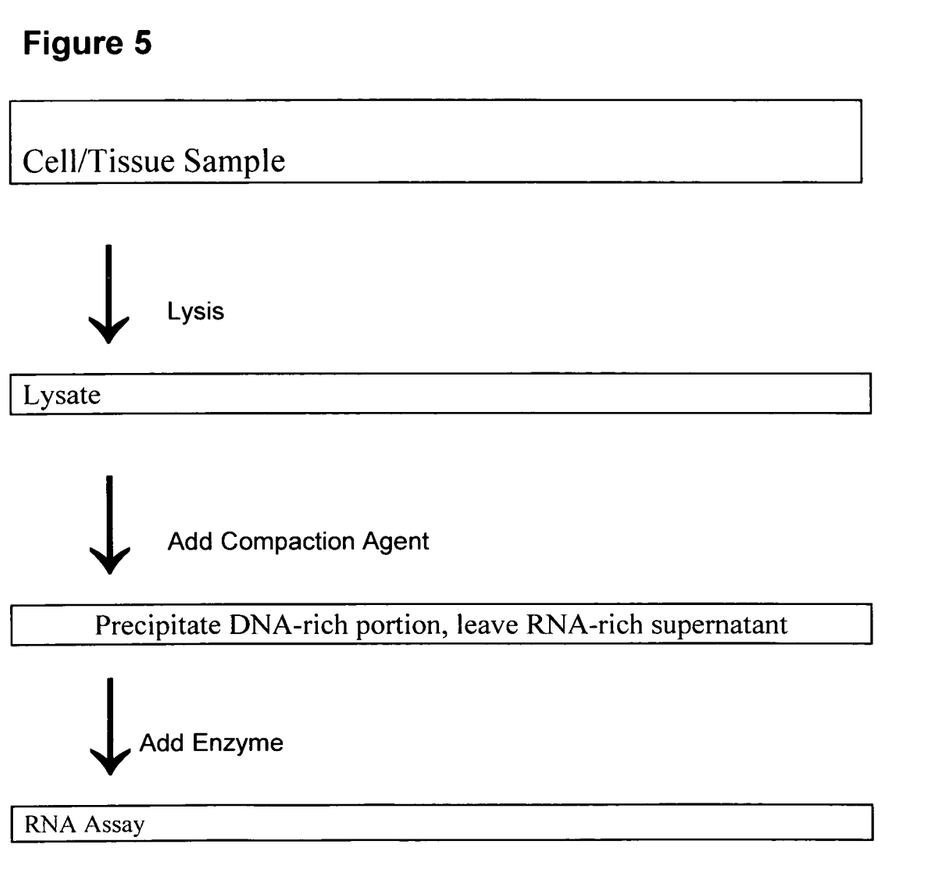
FIG. 5 shows a flow sheet of a preferred process of the invention

The plotted results (FIG. 4) show a classic titration curve with practically all the DNA removed from solution at a PZ6 concentration of about 22 micro molar.

EXAMPLE 13

Clearance of Preferred Compaction Agent from Solution with Ion-exchange Resin To 1.5 mL of a solution of 400 micro molar PZ6 in 25 mM MOPSO buffer, pH 6.8, 30 mM NaCl was added 67 milligrams of UnoSphere S cation-exchange resin (Biorad Corporation). The solution was mixed by vortexing for 1 minute, then centrifuged for 10 minutes at 7,200 g. The top 500 micro liter was removed and mixed with 500 microliter of a solution of Salmon DNA (50 micro gram per mL). The mixture was vortexed, centrifuged at 9,000 g, and the UV-visible absorbance was measured at 258 nm. The absorbance was 0.404 AU. The absorbance of the stock DNA solution itself was 0.823 AU. This result indicates that all of the PZ6 was removed by solution by the cation-exchange resin since the concentration of DNA insolution was that expected for a simple 1:1 dilution of the stock solution. This was further demonstrated by measuring the absorbance of a solution obtained by adding 500 micro liter of buffer to 500 micro liter of DNA stock solution. The absorbance of this solution was 0.415 AU.

A control experiment is performed as above except with no cation-exchange resin added. The absorbance of that solution at 258 nm was 0.01 AU indicating that practically all the added DNA had been precipitated.

These results confirm that cation-exchange resin can effectively remove PZ6 from solution.

EXAMPLE 14

Total RNA isolated from human cells is subjected to treatment with Quatroquat (Sachem, FIG. 2) to precipitate genomic DNA, centrifuged, and the supernatant subjected to RT-PCR.

Experimental Conditions: Reverse Transcription
1 ug of total human RNA (Stratagene)
1×RT Buffer
5.5 mM $MgCl_2$
500 µM per dNTP
2.5 µM Random Hexamers
0.4 U/µl Rnase Inhibitor
3.125 U/µl Multiscribe Reverse Transcriptase
Reaction volume: 20 µl
Thermal Profile: 10 min at 25° C.; 60 min at 37° C.; 5 min at 95° C.

The cDNA thus produced is amplified by PCR according to the following protocol:

Experimental Conditions: PCR
10 ng of cDNA (assuming 100% efficiency)
1×PCR Buffer
5 mM $MgCl_2$
200 µM per dNTP
500 nM of each of two beta-actin-directed primers.
2.5 U Tfi DNA Polymerase
Reaction volume: 50 µl
Thermal Profile: Activation: 3 min at 94° C.; (30 cycles) Denaturation: 45 sec at 94° C.; Annealing: 45 sec at 65° C.; Extension: 1 min at 72° C.; Last extension: 10 min at 72° C.

Gel electrophoresis shows that the expected 208 bp beta-actin product is formed. Separate experiments show that neither step in the RT-PCR process is inhibited by residual precipitant.

EXAMPLE 15

Plasmid DNA Precipitated and Purified

A culture of E. coli bacteria harboring a 6 kilobase plasmid encoding expressing a recombinant form of beta-interferon is subjected to alkaline lysis, and plasmid DNA precipitated with quatroquat, recovered by resuspension at high salt, and further purified by chromatography.

EXAMPLE 16

DNA Removal

Real-time PCR amplification of 2.5 ng of human DNA in 25 microliters gives Ct is 14.9 without compaction, and 22.0 after compaction precipitation with 0.5 uM Quatroquat. This change implies the removal of over 99% of genomic DNA. In a separate control experiment 4 uM concentration of quatroquat was shown not to inhibit the PCR reaction.

Modifications

Specific compositions, methods, or embodiments discussed are intended to be only illustrative of the invention disclosed by this specification. Variations on these compositions, methods, or embodiments are readily apparent to a person of skill in the art based upon the teachings of this specification and are therefore intended to be included as part of the inventions disclosed herein. For example, another potential application of selective precipitation is to the isolation and analysis of micro RNAs or proteins.

Most preferably, the invention comprises a method of preparing substantially purified RNA, without the use of DNAse or DNA adsorption, by adding an effective amount of a compaction agent to a sample so as to precipitate from said sample at least 90% of the genomic DNA and genomic DNA fragments.

Some Preferred Embodiments of the Invention Comprise:

A. A method of preparing substantially purified DNA, without the use of nucleases or proteases, by adding an effective amount of a compaction agent selected from the group consisting of: quaternary ammonium polyamines, the compounds of FIGS. 1-3 and PTCs to a lysate to precipitate, from said lysate, DNA having a content of RNA of less than 3% by weight.

B. A method for the production of purified DNA having a content of RNA of less than about 5% by weight, comprising in combination the following steps:
  A. lysing a cell mass to liberate the nucleic acids
  B. optionally precipitating some additional moieties.
  C. optionally adjusting the ionic strength and/or plasmid concentration and;
  D. precipitating a substantial fraction of the DNA away from RNA and protein by addition of an effective amount of a compaction agent.

selected from the group consisting of: quaternary ammonium polyamines, the compounds of FIGS. 1-3, and PTCs.
  E. Optionally washing the DNA-rich precipitate with a solution containing a precipitant other than a compaction agent.
  F. Optionally redissolving a fraction of the DNA-rich precipitate by exposure to a solution of ionic strength over 100 mM.

C. A method of preparing substantially purified protein, without the use of nucleases or proteases, by adding an effective amount of a compaction agent selected from the group consisting of: quaternary ammonium polyamines, the compounds of FIGS. 1-3 and PTCs to a mixture of protein and nucleic acids to precipitate, from said mixture, nucleic acids having a content of protein of less than 5% by weight.

D. The method of C above further comprising reducing the ionic strength of the mixture before addition of the compaction agent.

E. A composition of matter comprising DNA, substantially free of added nucleases, and containing less than about 3% by weight RNA and a compaction agent selected from the group consisting of: quaternary ammonium polyamines, the compounds of FIGS. 1-3 and PTCs.

F. A method of treatment of a mixture comprising RNA and DNA comprising mechanical lysis of the mixture in the presence of a compaction agent selected from the group consisting of: quaternary ammonium polyamines, the compounds of FIGS. 1-3 and PTCs to precipitate at least a portion of the DNA.

G. A composition of C above additionally comprising less than 0.0001 weight % RNAse.

H. A method of preparing substantially purified RNA without the use of nucleases or proteases, or organic solvent extraction, comprising adding an effective amount of a compaction agent selected from the group consisting of: quaternary ammonium polyamines, the compounds of FIGS. 1-3, and PTCs to a lysate containing DNA and RNA to selectively precipitate from said lysate, plasmid-DNA, chromosomal-DNA, or chromosomal DNA fragments having a content of less than 40% by weight RNA.

I. A method of preparing substantially purified DNA without the use of nucleases or proteases, or organic solvent extraction, comprising adding an effective amount of a compaction agent selected from the group consisting of: quaternary ammonium polyamines, the compounds of FIGS. 1-3, and PTCs to a lysate containing DNA and RNA to selectively precipitate from said lysate, plasmid-DNA, chromosomal-DNA, or chromosomal DNA fragments having a content of less than 40% by weight RNA.

J. A composition for the recovery of RNA comprising a mixture of combined reagents, one of which lyses and one of which precipitates DNA to produce and RNA sample reduced in DNA content.

K. A method according to B above for producing ribosomal RNA, chromosomal DNA, micro RNA, plasmid DNA, aptamers, artificial RNA, or mRNA or other natural or synthetic nucleic acids.

L. The method of A above comprising producing plasmid having an undetectable content of ribonucleases by standard assays.

M. The composition of E above additionally comprising a content of eukaryotic ribonucleases of less than 0.1% by weight.

N. The method of A above comprising producing plasmid having a content of eukaryotic ribonucleases of less than 0.001% by weight.

O. The method of A above in which the addition of the compaction agent comprises the addition of two or more different mixed compaction agents whereby improved separation efficiency results.

P. A method according to A above additionally comprising stripping the compaction agent by a stripping method selected from the group comprising high salt addition and/or a pH shift.

Q. A method according to B above additionally comprising stripping the compaction agent by a stripping method selected from the group comprising high salt addition and/or a pH shift.

R. A composition for the recovery of RNA comprising a mixture of combined reagents, one of which lyses and one of which precipitates DNA to clarify a cell mass.

S. A composition according to R above in which the lysing agent comprises a nonionic detergent.

T. A method according to B above in which lysing cells is accomplished at a low salt concentration, which is applied to lyse RNA-containing cells.

U. A method according to B above wherein the method is applied to remove large nucleic acid molecules from low ionic strength cell lysates.

V. A method according to B above additionally comprising a technique selected from the group consisting of: use of French cell press, addition of nonionic detergent, lysozyme addition, microfluidizer, freeze-thaw or any other relatively low ionic strength lysis technique to produce nucleic acid-reduced lysates for later protein recovery.

W. A method according to A above comprising simultaneous application of the method in parallel mini-prep procedures for a plurality of cell masses.

X. A method of assay comprising precipitating a labeled probe while it is hybridized to a target.

Y. A method according to B above additionally comprising a further separation step comprising one or more techniques selected from the group consisting of: precipitation and resuspension, filtration and adsorption for production of more pure product.

Z. A method of preparing substantially purified RNA without the use of nucleases or proteases, or organic solvent extraction, comprising adding an effective amount of a compaction agent selected from the group consisting of: quaternary ammonium polyamines, and PTCs to a lysate containing DNA and RNA to selectively precipitate from said lysate, plasmid-DNA, chromosomal-DNA, or DNA fragments having a content of RNA of less than 3% by weight.

AA. A method according to B above comprising addition of about 0.001 to 20 mM of a compaction agent selected from the group consisting of: basic polypeptides, polyamines, trivalent and tetravalent metal ions, manganese chloride, or the compounds of FIGS. 1-3.

BB. The method of B above wherein the cell mass comprises nucleic acid or a synthesized analog.

CC. The method of B above wherein the source of the lysate comprises gram-positive bacteria, yeast, eukaryotes, synthesized nucleic acids, Archaea, bacteria, protozoa, phages, other viruses, human cells, body fluids, mixtures of cells, tissues, or environmental samples.

DD. The method of B above wherein at least a portion of the unprecipitated compaction agent is removed by adsorption.

EE. A biotech kit comprising compaction agent and other reagents and apparatus designed for the purification of nucleic acids from lysates or synthetic solutions.

FF. A purification kit for plasmid DNA according to EE above comprised of lysis solutions, a resuspension solution, a compaction agent-based precipitation solution, a stripping solution and optionally a final resuspension solution.

GG. A purification kit for total RNA according to EE above comprised of a lysis solution; a $1^{st}$ compaction precipitation solution (which may be optionally combine with the lysis solution); a $2^{nd}$ compaction precipitation solution; a stripping solution; and optionally a final resuspension solution.

HH. A purification kit for chromosomal or genomic DNA according to EE above comprised of a lysis solution or solutions, a resuspension solution, a compaction agent-based precipitation solution, a stripping solution, and optionally a final resuspension solution.

II. A purification kit for large RNA fragments according to EE above comprised of a lysis solution; a $1^{st}$ compaction precipitation solution (which may be optionally combine with the lysis solution); a $2^{nd}$ compaction precipitation solution; a stripping solution; and optionally a final resuspension solution.

JJ. A purification kit for low molecular weight RNA fragments according to EE above comprised of a lysis solution; a $1^{st}$ compaction precipitation solution (which may be optionally combine with the lysis solution); a $2^{nd}$ compaction precipitation solution; a $3^{rd}$ compaction precipitation solution; a stripping solution; and optionally a final resuspension solution.

KK. A large-scale plasmid DNA purification kit according to EE above comprised of lysis solutions, a resuspension solution, a compaction agent-based precipitation solution, a stripping solution and optionally a final resuspension solution.

LL. A large-scale filtration-based plasmid DNA purification kit according to QQ above comprised of lysis solutions, a resuspension solution, a compaction agent-based precipitation solution, a stripping solution and optionally a final resuspension solution.

MM. A purification kit for RNA according to EE above comprised of lysis solutions, a compaction agent-based precipitation solution, and optionally a resuspension solution.

NN. A purification kit for total RNA according to EE above comprised of a lysis solution; a $1^{st}$ compaction precipitation solution (which may be optionally combined with the lysis solution); a $2^{nd}$ compaction precipitation solution; a stripping solution; and optionally a final resuspension solution.

OO. A purification kit for large RNA fragments according to EE above comprised of a lysis solution; a $1^{st}$ compaction precipitation solution (which may be optionally combine with the lysis solution); a $2^{nd}$ compaction precipitation solution; a stripping solution; and optionally a final resuspension solution.

PP. A purification kit for low molecular weight RNA fragments according to EE above comprised of a lysis solution; a $1^{st}$ compaction precipitation solution (which may be optionally combine with the lysis solution); a $2^{nd}$ compaction precipitation solution; a $3^{rd}$ compaction precipitation solution; a stripping solution; and optionally a final resuspension solution.

QQ. The use of filtration devices to enhance the speed and usability of kits listed in EE-PP above.

RR. Any of the above processes conducted in the presence of a poly quat compound.

SS. Any of the above processes conducted in the presence of a phosphonium compound.

TT. Any of the above processes conducted in the presence of a polyamine which is a quaternary compound.

UU. A nucleic acid separation process conducted in the presence of an ionic liquid, a phase transfer catalyst, or a polyamine or poly phosphonium, which is a quaternary compound.

VV. A composition of C above comprising less than about 0.1 Units endotoxin per microgram plasmid DNA (EU/ug or IE/ug).5b.

WW. A method according to B above producing a product comprising less than 0.3 Units endotoxin per microgram plasmid DNA (EU/ug or IE/ug).

XX. A composition of C above comprising less than 0.3 Units endotoxin per microgram plasmid DNA (EU/ug or IE/ug).

YY. A composition of C above comprising less than 0.1 Units endotoxin per microgram plasmid DNA (EU/ug or IE/ug).

Reference to documents made in the specification is intended to result in such patents or literature being expressly incorporated herein by reference.

TABLE A

| Parameter | Units | Preferred | Most Pref.+ |
|---|---|---|---|
| Cell Mass | | Archaea eukaryotes bacterial, Gram-negative Gram-positive phage, yeast, human, tissue, biopsy, mammalian | Gram-neg, human |
| Product: | | DNA, RNA, Assay NA-binding protein enzymes, cosmids, YACs, Plasmid Protein-containing lysate | assay RNA |
| C# of quat: | | 0.1-4 | 1-2 |
| q-value of quat: | | 1-4 | 1-2 |

Compaction Agent: basic polypeptides (e.g. polylysine), polyamines (e.g. protamine, spermidine, spermine, putrescine, cadaverine, etc.), trivalent and tetravalent metal ions (e.g. hexammine cobalt, chloropentammine cobalt, chromium (III)), netropsin, distamycin, lexitropans, DAPI (4',6 diamino 2-phenylindol), berenil, pentamidine, manganese chloride. More preferred: hexamine cobalt, spermine and spermidine. Most Preferred: Also, poly quaternary amines, poly amines and poly quaternary phosphoniums, poly ternary phosphoniums, compounds of FIGS. 1-3.

TABLE B

| | | |
|---|---|---|
| CA Conc. mM | 0.02-20 | 0.03-10 |
| Lysing Agent: | detergent nonionic det. BPER for RNA; (alkaline lysis is m.p. for plasmid DNA) | |
| " " Conc.: wt % | 0.5-2 | .05-.5 |
| pH: varies | 6-8 | 7 |
| Ionic Strength: mM (Before Compaction) | 0-200 | 0-50 |
| Endotoxin Level | >0.3 EU/mL | >0.1 EU/mL |
| RNA | mRNA, microRNA, ribozymes, messenger RNA riboswitches, ribosomal RNA | |
| RNA purity | <1 wt % gDNA | <0.1 wt % gDNA |
| DNA | DNA monomer nucleotides, cDNA copy of mRNA, plasmid DNA, cDNA, CDNA fragments, genomic DNA, genomic DNA fragments | |
| Enzymes | reverse transcriptase, helicase, DNA polymerase, RNA polymerase, nucleic acid-modifying enzymes active over 60 degrees C. | |
| Detection Method | PCR, NASBA, hybridization, RT-PCR Helicase chain reaction RT-PCR | |

The polyquaternary ammonium compounds of the instant invention include those having the formula (I):

TABLE C

Ionic Compounds

In certain situations, ionic compounds can act as phase-transfer catalysts/compaction agents, particularly when they are a form of N-quats. These materials are liquid at the reaction temperature, typically under 100° C. and preferably include:

Tetrapropyl Ammonium Bromide
Tetrapropyl Ammonium Chloride
Tetrapropyl Ammonium Hydroxide
Tributyl Methyl Ammonium Chloride
Triethyl Benzyl Ammonium Chloride]

TABLE D

Quaternary Phosphonium Salts

Benzyl Triphenyl Phosphonium Bromide
Benzyl Triphenyl Phosphonium Chloride
Butyl Triphenyl Phosphonium Bromide
Butyl Triphenyl Phosphonium Chloride
Ethyl Triphenyl Phosphonium Acetate
Ethyl Triphenyl Phosphonium Bromide
Ethyl Triphenyl Phosphonium Iodide

STRUCTURE I $An^-$

Wherein:

each group $R_1$, $R_2$, $R_3$, $R'_1$, $R'_2$, $R'_3$, $R_4$ and $R_5$ may be independently selected from alkyl, aryl, and a alkyl; and each contain preferably 1-10, more preferably 1-6 C-atoms.

each Y may be independently selected from —H, —OH, halo, alkyl, aryl and a alkyl, preferably —OH, and each contains preferably 0-10, more preferably 0-6 C-atoms;

z may be any whole number from 0 to about 10, more preferably 1-6;

a, b, and c each may be any whole number from 0 to 2, with the proviso that the sum a+b+c in any fragment is at least 1; and $An^-$ may be one of more organic or inorganic, monovalent or polyvalent anion as needed to obtain a neutral compound e.g. chloride, hydroxide, acetate.

Specific examples of quaternary nitrogen cations represented by Structure I include N,N,N,N',N',N'-hexamethyl-methylenediammonium; N,N,N,N',N',N'-hexabutyl-1,4-butylenediammonium; N,N,N,N',N',N'-hexabutyl-1,6-hexamethylenediammonium;N,N,N,N',N',N'-hexabutyl-1,4-phenylenediammonium; etc.

TABLE D-continued

Quaternary Phosphonium Salts

Methyl Triphenyl Phosphonium Bromide
Tetrabutyl Phosphonium Bromide
Tetraphenyl Phosphonium Bromide

What is claimed is:

1. A method of assaying a target RNA in a mixture comprising DNA and RNA, said method comprising in combination the steps of:
   A. precipitating a DNA-rich portion, leaving an RNA-rich portion, without the use of nucleases or proteases or organic solvent extraction, by adding a compaction agent to effect compaction precipitation;
   B. catalyzing a reaction dependent on the presence of the target RNA by adding an enzyme to the RNA-rich portion to catalyze the reaction; and
   C. detecting and assaying a product of the reaction catalyzed by the enzyme, as an indicator of the target RNA.

2. The method of claim 1 wherein the reaction comprises messenger-RNA (mRNA) and DNA monomer nucleotides to produce cDNA under the action of reverse transcriptase.

3. The method of claim 1 wherein the cDNA is a copy of the mRNA, reverse-transcribed into DNA form by a template-guided polymerization.

4. The method of claim 1 wherein the product is detected by methods comprising Polymerase Chain Reaction (PCR).

5. The method of claim 1 wherein the compaction agent is selected from the group consisting of: basic polypeptides, polyamines, netropsin, distamycin, lexitropans, DAPI (4',6 diamino 2-phenylindol), berenil, pentamidine, manganese chloride, hexammine cobalt, spermine and spermidine, poly quaternary ammnonium compounds, poly amines, poly quaternary phosphoniums, and ternary polyphosphines, the compounds of FIGS. 1, 2 and 3 and Tetrapropyl Ammonium Bromide, Tetrapropyl Ammonium Chloride, Tetrapropyl Ammonium Hydroxide, Tributyl Methyl Ammonium Chloride, Triethyl Benzyl Ammonium Chloride, Benzyl Triphenyl Phosphonium Bromide, Benzyl Triphenyl Phosphonium Chloride, Butyl Triphenyl Phosphonium Bromide, Butyl Triphenyl Phosphonium Chloride, Ethyl Triphenyl Phosphonium Acetate, Ethyl Triphenyl Phosphonium Bromide, Ethyl Triphenyl Phosphonium Iodide, Methyl Triphenyl Phosphonium Bromide, Tetrabutyl Phosphonium Bromide and Tetraphenyl Phosphonium Bromide.

6. The method of claim 5 wherein the polyamine comprises a polyquaternary ammnonium compound.

7. The method of claim 1 wherein the enzyme is selected from the group consisting of reverse transcriptase, helicase, DNA polymerase, RNA polymerase, and nucleic acid modifying enzymes retaining substantial activity above 60 degrees C.

8. The method of claim 1 wherein the RNA comprises an RNA selected from the group consisting of messenger RNA, microRNA, ribozymes, riboswitches, and ribosomal RNAs.

9. The method of claim 2 wherein the polyamine comprises a compound having a structure of FIG. 1.

10. The method of claim 1 wherein the compaction agent comprises a compound selected from the group consisting of Tetrapropyl Ammonium Bromide, Tetrapropyl Ammonium Chloride, Tetrapropyl Ammonium Hydroxide, Tributyl Methyl Ammonium Chloride, Triethyl Benzyl Ammonium Chloride, Benzyl Triphenyl Phosphonium Bromide, Benzyl Triphenyl Phosphonium Chloride, Butyl Triphenyl Phosphonium Bromide, Butyl Triphenyl Phosphonium Chloride, Ethyl Triphenyl Phosphonium Acetate, Ethyl Triphenyl Phosphonium Bromide, Ethyl Triphenyl Phosphonium Iodide, Methyl Triphenyl Phosphonium Bromide, Tetrabutyl Phosphonium Bromide and Tetraphenyl Phosphonium Bromide.

11. The method of claim 1 further comprising removing at least a portion of the unprecipitated compaction agent after Step A.

12. The method of claim 1 wherein the product is an RNA product comprising less than 1 wt % gDNA content.

13. The method of claim 1 for preparing a substantially purified RNA having a genomic DNA content of less than 1% and a substantially purified DNA having an RNA content of less than 10% without the use of nucleases or proteases or organic solvent extraction, comprising adding an effective amount of a compaction agent selected from the group consisting of: quaternary ammonium polyamines, and Phase Transfer Catalysts (PTCs) to a lysate containing DNA and RNA to selectively precipitate from said lysate, a DNA selected from the group consisting of: plasmid-DNA, chromosomal-DNA, and chromosomal DNA fragments wherein said DNA has an RNA content of less than 10%.

14. The method of claim 1 wherein the compaction agent is selected from the group consisting of polylysine, protamine, spermidine, spermine, putrescine, cadaverine, hexammine cobalt, chloropentammine cobalt, and chromium (III) compounds.

15. The method of claim 1 wherein the compaction agent comprises a polyquaternary ammonium compound.

16. A method of assaying a target RNA in a mixture comprising DNA and RNA, said method comprising in combination the steps of:
   A. precipitating a DNA-rich portion, leaving an RNA-rich portion without the use of nucleases or proteases or organic solvent extraction, by adding a compaction agent comprising a polyquaternary ammonium compound to effect compaction precipitation;
   B. catalyzing a reaction dependent on the presence of the target RNA by adding an enzyme to the RNA-rich portion to catalyze the reaction; and
   C. detecting and assaying a product of the reaction catalyzed by the enzyme, as an indicator of the target RNA.

17. The method of claim 16 wherein the source of the mixture is a lysate comprising gram-positive bacteria, yeast, eukaryotes, synthesized nucleic acids, Archaea, bacteria, protozoa, phages, other viruses, human cells, body fluids, mixtures of cells, tissues, or environmental samples.

18. The method of claim 16 wherein the enzyme is selected from the group consisting of reverse transcriptase, helicase, DNA polymerase, RNA polymerase, and nucleic acid modifying enzymes.

19. The method of claim 16 wherein the RNA comprises an RNA selected from the group consisting of messenger RNA, microRNA, ribozymes, riboswitches, and ribosomal RNAs.

20. A method of assaying a target RNA in a mixture comprising DNA and RNA, said method comprising in combination the steps of:
   A. precipitating a DNA-rich portion without the use of nucleases or proteases or organic solvent extraction, leaving an RNA-rich portion, by adding a compaction agent comprising a polyquaternary ammonium compound to effect compaction precipitation;
   B. catalyzing a reaction dependent on the presence of the target RNA by adding an enzyme to the RNA-rich portion to catalyze the reaction; and
   C. detecting and assaying a product of the reaction catalyzed by the enzyme, as an indicator of the target RNA;
   wherein the enzyme is selected from the group consisting of reverse transcriptase, helicase, DNA polymerase, RNA polymerase, and nucleic acid modifying enzymes and wherein the RNA comprises an RNA selected from the group consisting of messenger RNA, microRNA, ribozymes, riboswitches, and ribosomal RNAs and wherein the source of the mixture is a lysate which comprises gram-positive bacteria, yeast, eukaryotes, synthesized nucleic acids, Archaea, bacteria, protozoa, phages, other viruses, human cells, body fluids, mixtures of cells, tissues, or environmental samples.

* * * * *